US00PP27156P2

(12) United States Plant Patent
van Noort

(10) Patent No.: US PP27,156 P2
(45) Date of Patent: Sep. 13, 2016

(54) ***COREOPSIS* PLANT NAMED 'SOLAR DANCE'**

(50) Latin Name: ***Coreopsis* hybrid**
Varietal Denomination: Solar Dance

(71) Applicant: Marco van Noort, Warmond (NL)

(72) Inventor: Marco van Noort, Warmond (NL)

(73) Assignee: Marco van Noort Breeding BV, Warmond (NL)

( * ) Notice: Subject to any disclaimer, the term of this patent is extended or adjusted under 35 U.S.C. 154(b) by 168 days.

(21) Appl. No.: 14/121,873

(22) Filed: Oct. 29, 2014

(51) Int. Cl.
*A01H 5/02* (2006.01)

(52) U.S. Cl.
USPC ..... Plt./417

(58) Field of Classification Search
USPC ..... Plt./417
See application file for complete search history.

*Primary Examiner* — Keith Robinson
(74) *Attorney, Agent, or Firm* — Penny J. Aguirre

(57) ABSTRACT

A new cultivar of hybrid *Coreopsis* named 'Solar Dance' that is characterized by its broadly upright and compact plant habit, its semi-double ray florets that are deep yellow in color, its long and floriferous bloom period, its good winter hardiness compared to other cultivars of *Coreopsis*, and its healthy foliage.

2 Drawing Sheets

Botanical classification: *Coreopsis* hybrid.
Variety denomination: 'Solar Dance'.

BACKGROUND OF THE INVENTION

The present invention relates to a new and distinct cultivar of a plant botanically of hybrid origin and known as *Coreopsis*. The new cultivar will be referred to hereafter by its cultivar name 'Solar Dance'. 'Solar Dance' is an herbaceous perennial grown for landscape and container use.

'Solar Dance' was selected by the Inventor as a seedling in a trial garden in Warmond, The Netherlands in July of 2011. The new cultivar arose from open pollination of an unnamed (not patented) seedling of *Coreopsis grandiflora* in the inventors breeding program. The male parent is unknown but the new cultivar is believed to be of hybrid origin rather than a cultivar of *Coreopsis grandiflora*.

Asexual propagation of the new cultivar was first accomplished by root cuttings in Warmond, The Netherlands in February of 2014 by the Inventor. Asexual propagation by root cuttings and stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Solar Dance' as unique cultivar of *Coreopsis*.

1. 'Solar Dance' exhibits a broadly upright and compact plant habit.
2. 'Solar Dance' exhibits semi-double ray florets that are deep yellow in color.
3. 'Solar Dance' exhibits a long and floriferous bloom period.
4. 'Solar Dance' exhibits good winter hardiness.
5. 'Solar Dance' exhibits healthy foliage.

The female parent of 'Solar Dance', an unnamed *Coreopsis grandiflora* seedling, differs from 'Solar Dance' in having a more open plant habit, in having fewer ray florets, in having a shorter bloom period, and in being less floriferous. 'Solar Dance' can be compared to the *Coreopsis* cultivars 'Galaxy' (U.S. Plant Pat. No. 21,999) and 'Moonbeam' (not patented). 'Galaxy' is similar to 'Solar Dance' in having semi-double ray florets. 'Galaxy' differs from 'Solar Dance' in having a more open plant habit, in being less floriferous, and in having ray florets that are lighter yellow in color. 'Moonbeam' is similar to 'Solar Dance' in being cold hardy to U.S.D.A Zone 4. 'Moonbeam' differs from 'Solar Dance' in having ray florets that are darker yellow in color, in having single ray florets, and in having leaves that are narrower in width.

BRIEF DESCRIPTION OF THE DRAWINGS

The accompanying colored photographs illustrate the overall appearance and distinct characteristics of the new *Coreopsis*. The photographs were taken of four month-old plants of 'Solar Dance' as field grown in Warmond, The Netherlands and placed in a container for the photographs.

The photograph in FIG. 1 provides a side view of 'Solar Dance' in bloom.

Figure 1:
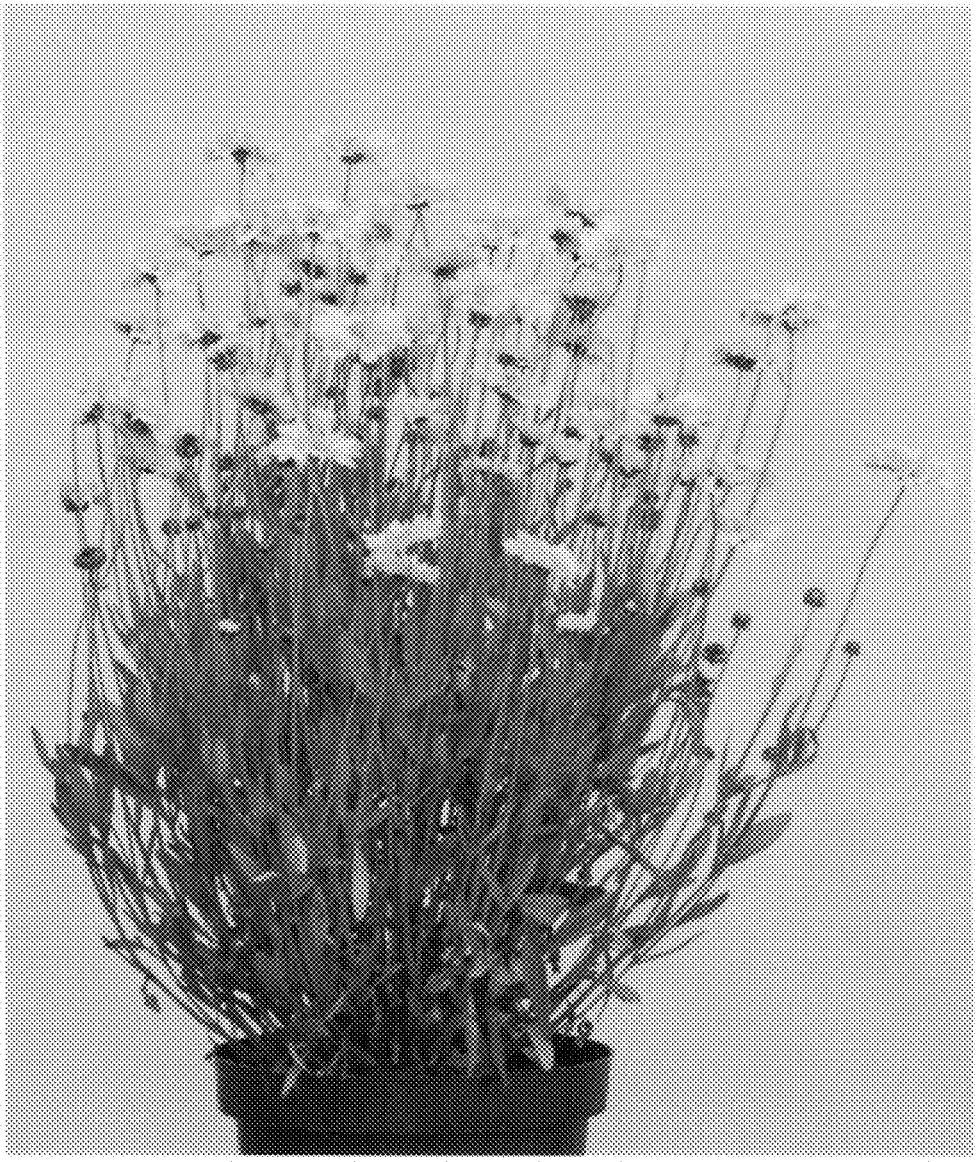
Figure 2:
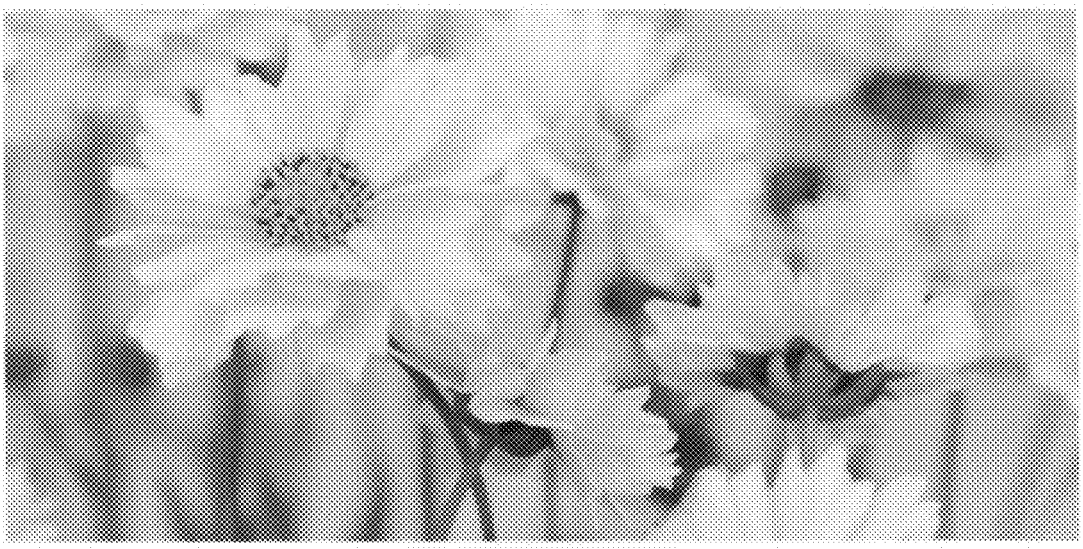

The photograph in FIG. 2 provides a close-up view of the inflorescences of 'Solar Dance'.

Figure 3:
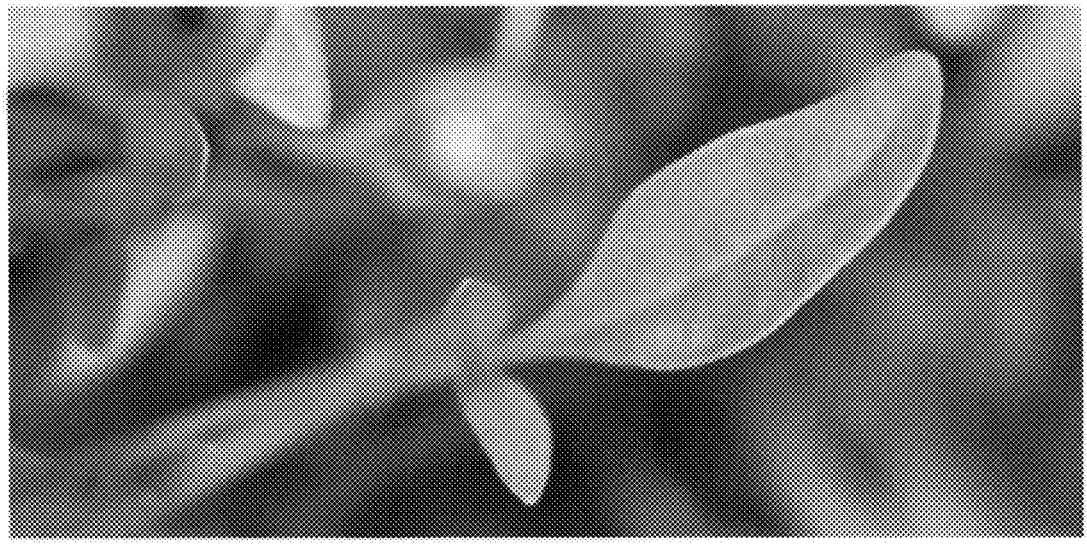

The photograph in FIG. 3 provides a close-up view of a leaf of 'Solar Dance'.

The colors in the photographs are as close as possible with the photographic and printing technology utilized and the color values cited in the detailed botanical description accurately describe the colors of the new *Coreopsis*.

DETAILED BOTANICAL DESCRIPTION

The following is a detailed description of four month-old plants of the new cultivar as field grown outdoors in Warmond, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms from June to late September in the Netherlands.

*Plant habit*.—Herbaceous perennial, broadly-upright, clump-forming, densely branched.

*Height and spread*.—An average of 50 cm in height and in width.

*Cold hardiness*.—At least in U.S.D.A Zone 4.

*Diseases*.—Plants have been observed to be healthy without any disease problems observed.

*Root description*.—Fibrous when young, becoming fleshy with age.

*Propagation*.—Root cuttings and stem cuttings.

*Growth rate*.—Moderate.

Stem description:

*Shape*.—Oval, ridged.

*Stem color*.—144A.

*Stem size*.—Main and secondary stems; an average of 16.4 cm in length and 2.5 mm in width.

*Stem surface*.—Glabrous.

*Stem aspect*.—Upright.

*Branching habit*.—Well-branched, an average of 1 main branch, 105 secondary branches per main stem.

*Internode length*.—An average of 5.6 cm.

Foliage description:

*Leaf division*.—Simple.

*Leaf margins*.—Entire to trifid.

*Leaf size*.—Variable, up to 6.4 cm in length and 1.3 cm in width when entire, up to 6.4 cm in length and 2.6 cm in width when trifid.

*Leaf shape*.—Lanceolate when entire and hastate when trifid.

*Leaf base*.—Long cuneate.

*Leaf apex*.—Broadly acute.

*Leaf venation*.—Pinnate, color on the upper surface; N144A and on the lower surface; 146C.

*Leaf attachment*.—Sessile.

*Leaf arrangement*.—Opposite.

*Leaf surface*.—Upper and lower surface dull, lower surface base, margins and main vein sparsely pubescent with very short soft hairs an average of 0.3 mm in length and NN155D in color.

*Leaf color*.—Young and mature upper surface; 144A, young lower surface; 146B, mature lower surface; 146D.

Inflorescence description:

*Inflorescence type*.—Solitary capitulum consisting of disc florets surrounded by two rows of ray florets.

*Lastingness of inflorescence*.—An average of 3 weeks until senescence of ray flowers, longer in cool temperatures, bracts and disk flowers are persistent.

*Fragrance*.—None.

*Quantity of inflorescences*.—An average of 2 per lateral stem.

*Inflorescence size*.—An average of 2 cm in depth an average of 4.4 cm in diameter.

*Inflorekence buds*.—Average of 7 mm in depth and 9 mm in diameter, flattened globular in shape, color; 152A with apex 3A.

*Peduncle*.—Oval in shape, an average of 18.6 cm in length and 2 mm in width, glabrous, slightly glossy surface, N144A to N144C in color.

*Sepals*.—An average of 5, 8 mm in length and 2 mm in width, N144A to N144C in color.

Involucral bracts:

*Bract number*.—An average of 18, 10 outer bracts and 8 inner bracts.

*Bract arrangement*.—Bracts surround receptacle in a campanulate form, held close to lower surface of ray florets.

*Bract size*.—Outer bracts; an average of 1 cm in length and 5 mm in width, lower bracts; an average of 6 mm in length and 4 mm in width.

*Bract color*.—Outer bracts upper and lower surface; 152A with margins 153C to 153D, inn bracts upper surface; 143C and lower surface; 143B.

*Bract texture*.—Surface of outer bracts; glabrous and dull and inner bracts; glabrous and slightly glossy.

*Bract apex*.—Acute.

*Bract base*.—Broad cuneate.

*Bract margins*.—Entire.

*Bract shape*.—Outer bracts; deltoid, inner bracts; ovate.

Ray florets (sterile):

*Number*.—An average of 18 arranged primarily in two rows.

*Shape*.—Obcordate.

*Size*.—An average of 2.1 cm in length and 1.5 cm in width.

*Apex*.—4 notched, lobes acute.

*Base*.—Cuneate.

*Margins*.—Entire with apex notched.

*Arrangement*.—Rotate and outward.

*Texture*.—Glabrous and dull on upper and lower surface, upper surface slightly velvety.

*Color*.—When opening inner surface; 5B with base 7A and outer surface; 7A with base 12A, when fully open inner surface; 9A with the base 12A and outer surface; 7A with the base 12A.

Disk flowers (perfect):

*Shape*.—Tubular, corolla is fused, flared at apex.

*Number*.—About 70.

*Size*.—About 8 mm in length and 0.5 mm in width.

*Color*.—En masse; 14A, corolla tube; 15B with base 145C and apex 14A.

*Receptacle*.—About 5 mm in diameter and 2 mm in depth, color; 145C.

Reproductive organs:

*Presence*.—Disk flowers are perfect, ray flowers are sterile.

*Gynoecium*.—1 Pistil, 7 mm in length, style is very fine, 5.5 mm in length and 15C in color, stigma is decurrent in shape and 15A in color, ovary is 1 mm in length and width, inferior, and 145D in color.

*Androcoecium*.—5 stamens, fused into tube surrounding style, anther; an average of 4 mm in length, basifixed and linear in shape, 14A with base 200A in color, pollen is moderate in quantity and 17B in color.

*Fruit/seed*.—No fruit or seed development was observed.

It is claimed:

1. A new and distinct cultivar of *Coreopsis* plant named 'Solar Dance' as herein illustrated and described.

* * * * *